United States Patent
Swaak

(10) Patent No.: US 9,155,782 B2
(45) Date of Patent: *Oct. 13, 2015

(54) USE OF ERYTHROPOIETIN IN THE TREATMENT OF CHRONIC INFLAMMATION

(75) Inventor: Anthonius Josef Swaak, Rotterdam (NL)

(73) Assignee: Roche Diagnostics GMBH, Mannheim (DE)

( * ) Notice: Subject to any disclaimer, the term of this patent is extended or adjusted under 35 U.S.C. 154(b) by 1148 days.

This patent is subject to a terminal disclaimer.

(21) Appl. No.: 11/811,665

(22) Filed: Jun. 11, 2007

(65) Prior Publication Data

US 2007/0249525 A1    Oct. 25, 2007

Related U.S. Application Data

(63) Continuation of application No. 08/817,704, filed on Aug. 25, 1997, now Pat. No. 7,344,717.

(30) Foreign Application Priority Data

Nov. 3, 1994 (EP) ..................................... 94203205

(51) Int. Cl.
*A61K 39/00* (2006.01)
*A61K 38/18* (2006.01)

(52) U.S. Cl.
CPC .................................. *A61K 38/1816* (2013.01)

(58) Field of Classification Search
None
See application file for complete search history.

(56) References Cited

FOREIGN PATENT DOCUMENTS

EP    0 269 394    6/1988
GB    2171304 A    8/1986

OTHER PUBLICATIONS

Swaak et al., Clin. Exp. Rheumatol. 1994, pp. 577.
Toshihide, et al., Kyushu Riumachi, Kyushu Journal of Rheumatology, 1991, pp. 19-23, vol. 10, No. 1, English Abstract Only.
Petterson et al., Scandinavian Journal of Rheumatology, 1993, pp. 188-193, vol. 22, No. 4.
Biemond et al., Chemical Abstracts, Iron Mobilization From Ferritin by Superoxide Derived From Stimulated Polymorphonuclear, Jul. 16, 1994, vol. 101, No. 3.
Vreugdenhil et al., Iron Stores and Serum Transferrin Receptor Levels During Recombinant Human Erythropoietin, Dec. 1992, pp. 265-268, vol. 65, No. 6.
Peeters et al., Effects of Recombinant-Human Erythropoietin on Anaemia and Disease Activity in Patients, Sep. 1995, pp. S288, vol. 38, No. 9.
Robbins Pathologic Basis of Disease, 4th edition, 1989, pp. 190-193.
Smilek et al., A signle amino acid change in a myelin basic protein peptide confers the capacity to prevent rather than induce EAE, PNAS, 1991, pp. 9633-9637, vol. 88.
Petrova, From the Amazon to the Alps: A Comparison of the Pharmaceutical Biodiversity Legal Protection in Brazil and Switzerland, 15 Pace Int'l L. Rev. 247, pp. 247-281, 2003, Pace University School of Law.
Martin, Patentability of Methods of Medical Treatment, 82 J. Pat & Trademark Off. Soc'y 381, pp. 381-423, 2000, Patent and Trademark Office Society.

*Primary Examiner* — Gerald R Ewoldt
(74) *Attorney, Agent, or Firm* — TraskBritt, P.C.

(57) ABSTRACT

A novel use of the known protein erythropoietin (EPO), and/or a derivative, and/or a fragment thereof, is disclosed. EPO is used as a pharmaceutical for the treatment of chronic inflammations. A particularly beneficial result is seen in patients suffering from rheumatoid arthritis (RA). Significant effects are seen in clinical variables such as morning stiffness, swollen joints, and the like.

2 Claims, No Drawings

USE OF ERYTHROPOIETIN IN THE TREATMENT OF CHRONIC INFLAMMATION

CROSS-REFERENCE TO RELATED APPLICATIONS

This application is a continuation of U.S. patent application Ser. No. 08/817,704, filed Aug. 25, 1997, now U.S. Pat. No. 7,344,717, which application is a U.S. national phase entry under 35 U.S.C. §371 of International Patent Application PCT/NL95/00370, filed Oct. 26, 1995, published in English as International Patent Publication WO 96/14081 on May 17, 1996, which claims the priority benefit of European Patent Application Serial No. 94203205.3 filed Nov. 3, 1994, the entire contents of each of which are hereby incorporated herein by this reference.

TECHNICAL FIELD

The invention relates to certain novel uses of the known protein erythropoietin (EPO), or substances having such activity as disclosed herein.

BACKGROUND

Erythropoietin is a humoral regulator of erythropoiesis, which stimulates the production of erythrocytes. In normal conditions it is produced in sufficient quantities in the kidneys and the liver.

In case of hypoxic shock (such as massive blood loss), erythropoietin production needs to be increased, which means that it has to be synthesized de novo. In disease-free conditions, erythropoietin levels in circulation are extremely low.

Certain diseases or side effects of treatments of certain diseases lead to a chronic anemia that overcharges the capacity of erythropoietin production, or otherwise cannot be met by the body's own erythropoietin resources. These diseases include chronic insufficiency of the kidneys, anemias associated with malignancies, neonate anemia, chronic anemia associated with rheumatoid arthritis (ACD), anemia after bone marrow transplantation, aplastic anemia, myeloplastic syndrome and various hemoglobin-related diseases. Also anemic side effects have been shown to occur in various chemotherapies and AZT-therapy. In these cases, it may be helpful to administer EPO to increase erythrocyte production.

Human EPO is available as a recombinant protein, which ensures that sufficient quantities can be produced in a very pure form.

Several studies with recombinant human erythropoietin (r-hu-Epo) have been carried out, mainly in patients who underwent renal dialysis for chronic renal failure, in which diminished production of Epo and severe anemia requiring regular blood transfusions occur. A correction of anemia by r-hu-Epo was shown in these cases with minimal side effects.[16,17,18] In AIDS patients treated with Zidovudine causing bone marrow suppression, administration of 100 U r-hu-Epo/kg thrice weekly intravenously significantly decreased transfusion requirements.[19]

The invention provides a novel use of erythropoietin that is not directly related to its erythrocyte-stimulating properties. This use is specifically clear in rheumatoid arthritis, which, therefore, is more specifically described in an explanatory example for the invention.

Rheumatoid arthritis is an inflammatory disease of synovial membranes, usually expressing itself in a symmetrical polyarthritis. During the course of their disease, 70% of rheumatoid arthritis (RA) patients develop some kind of anemia,[1] which may be due to iron deficiency,[2,3] vitamin B12 deficiency or folic acid deficiency,[4,5] hemolysis or adverse reactions to anti-rheumatic drugs.[6,7] In addition, active RA is frequently (in nearly 50%) accompanied by anemia of chronic disease (ACD).[8]

Factors involved in the pathogenesis of ACD are ineffective erythropoiesis,[9] interleukin-1,[10] tumor necrosis factor a (TNF-α),[11] decreased erythropoietin synthesis[5,12,13] and/or a decreased response to erythropoietin by the bone marrow.[14,15]

So far, only a few studies with r-hu-Epo have been carried out in RA patients. A hemoglobin (Hb) rise was shown in two anemic RA patients treated with r-hu-Epo, 125-250 IU/kg thrice weekly, a significant hematocrit rise was recorded.[20]

We have treated ten RA patients who suffered from ACD with recombinant human EPO.

In all RA patients, a rise in hemoglobin was observed. Despite a wide range of values, the increase in hemoglobin became significant after the second week of treatment with recombinant human EPO.

Besides this expected result of EPO treatment, a different unexpected benefit was obtained by the treatment.

DISCLOSURE OF THE INVENTION

The invention thus provides the use of erythropoietin or a substance having erythropoietin-like activity in the preparation of a pharmaceutical for the treatment of chronic inflammations, especially those related to (auto-) immune diseases, in particular RA. In RA, we found an overall improvement in the clinical parameters for scoring disease activity. Most impressive are the results on clinical variables such as pain score and morning stiffness as disclosed below. A significant decrease in the number of tender joints was already observed after two weeks of treatment. The changes in other clinical parameters did not reach statistical significance due to the wide range of values and the small number of patients in the study. However, when the parameters were expressed as percentages of their baseline value, significant improvements were observed.

In addition to this effect on clinical variables, a further positive effect was seen in the area of an overall sense of well-being of the treated patients.

According to the invention, any erythropoietin that has the ameliorating effect on chronic inflammations can be used. Preferably, this erythropoietin is not immunogenic so that it can be administered repeatedly. This will usually lead to the use of human erythropoietin of any origin, although recombinant erythropoietin seems the product of choice because of its purity and constant quality. On the other hand, it may very well be possible to use non-human truncated forms of mammalian erythropoietin as long as they have the activity and are not immunogenic upon normal administration to patients. Selected mutants (longer acting, more stable), fragments or derivatives of erythropoietin may also be used as long as they fulfill both criteria.

It is worthwhile to note that patients not having a kind of anemia can thus be treated with EPO. However, caution has to be taken that Hb levels do not rise to detrimental levels. Ways of lowering the Hb levels are well known in the art.

Also, it will be necessary to ensure that no hypertension occurs at a detrimental level. Ways to avoid such a reaction are also well known in the art.

One of the mechanisms through which EPO may ameliorate the disease symptoms in RA (or other chronic inflammations) is that it mobilizes iron towards hemoglobin production. Iron (free and/or bound in ferritin) deposits are known to occur in the synovia of RA-affected patients. Synovial fluid iron levels correlate with RA activity and, therefore, it is thought that iron is involved in the initiation or maintenance of RA synovitis through mediating tissue damage. The role of iron in the pathogenesis of RA may be related to the fact that iron stimulates the production of hydroxyl radicals, which are very potent agents in the destruction of cartilage, membranes and proteins. A thorough discussion of the role and the mechanisms of iron in the inflamed joint can be found in Vreugdenhil et al.[23] In this study, it is suggested to administer iron chelators to RA patients. EPO does not chelate iron. However, EPO does mobilize iron to be incorporated into hemoglobin through serum transferrin. Thus, EPO may reduce the levels of iron in the synovial fluids.

Another possible mechanism that may be responsible for the unexpected beneficial effect of EPO in (especially) RA, may be found in its influence on the $T_{h1}/T_{h2}$ balance.

One of the key functional parameters determining the outcome of immune responses, for example, infectious agents, is the nature of the cytokines produced locally by immune cells. At this moment, evidence is obtained that T-cells can be classified into $T_{h1}$ and $T_{h2}$ cells; both characterized by a different cytokine secretion profile. $T_{h1}$ cells secrete IL-2 and TNF-γ upon activation, but not IL-4 or IL-5, and $T_{h2}$ cells produce IL-4 and IL-5 but not IL-2 or TNF-γ. The differential cytokine profile of these CD4+T cells correlates with different effector functions exerted by these cells: $T_{h1}$ cells mediate delayed type hypersensitivity (DTH) responses and $T_{h2}$ provide superior help for antibody productions by B cells. There is also some support for the notion that $T_{h1}$ and $T_{h2}$ cells are progeny of $T_{h0}$ cells that can produce IL-2, TNF-γ, IL-4 and IL-5 simultaneously. $T_{h1}$ like cytokine secretion profile. In different animal studies and observations in human diseases, like leprosy, evidence is obtained that the balance between $T_{h1}$ and $T_{h2}$ response determined the outcome of, for example, an infectious disease and disease manifestations. At this moment, a selective activation of $T_{h1}$-like T cells is proposed as a hallmark of the ethiopathogenesis of rheumatoid arthritis. Evidence for this hypothesis is formed by the fact that on histopathological examination of the synovial tissue, a DTH-like inflammatory reaction is observed that is characteristic for a $T_{h1}$ response.

Some observations in our RA patients treated with r-hu-EPO showed a rise in serum IgE levels, which is consistent with the concept that EPO can give support for a $T_{h2}$-like response. In other ways, influencing the $T_{h1}$-$T_{h2}$ balance in a more $T_{h2}$ cytokine secretion profile. Indirect evidence for this hypothesis is formed by the fact that two out of three monoclonals raised against EPO are of the IgE class (IgE synthesis is regulated by IL-4).

When EPO is administered to newborn rats, a reduced neutrophil production is observed. This reduced neutrophil production may be partly responsible for the ameliorating effect observed in our patients in that neutrophils play a key role in inflammatory reactions.

It has also been observed that EPO can in some ways counteract the activity of TNF-α. TNF-α is an important pro-inflammatory cytokine.

It may also be the case that EPO diverts the multipotent progenitor blood cells to the production of erythrocytes instead of granulocytes.

DETAILED DESCRIPTION OF THE INVENTION

Experimental
Patients

This study focused on the effects of r-hu-Epo on RA disease activity parameters. It is a part of a project studying the pathogenesis of ACD and possible therapeutic strategies. The effect of r-hu-Epo on the anemia and iron metabolism is reported in more detail.[21]

Ten patients with RA[22] were studied, fulfilling the criteria for ACD as proposed by Cartwright.[8] ACD was confirmed by measuring stainable iron in a bone marrow preparation. Patients treated previously with iron, vitamin B12, folic acid and cytotoxic drugs were excluded. Other causes of anemia were also excluded, such as the presence of hematuria, positive occult blood test in stool, decreased creatinine clearance, hemolysis and low vitamin B12 or folic acid.

The demographic features of the studied patients are summarized in Table I. All patients used a variety of non-steroidal anti-inflammatory drugs.

Treatment

Recombinant human Erythropoietin (r-hu-Epo, Boehringer, Mannheim, Germany), was administered three times a week at a dose of 240 units/kg subcutaneously at the right upper leg for six weeks.

Clinical and Laboratory Monitoring

Detailed clinical and laboratory evaluation was performed at entry and weekly by the same physician, until the end of the study (six weeks), then at nine and twelve weeks after onset of the study. Routine laboratory procedures were used for assessment of hemoglobin (Hb), hematocrit (Ht), mean corpuscular volume (MCV), mean corpus hemoglobin (MCH) and reticulocytes count. Serum iron was measured spectrophotometrically (Instruchemie, Hilversum, the Netherlands). Transferrin and CRP was assessed with a nephelometer (Ablon Medical Systems, Leusden, the Netherlands) and serum ferritin by solid phase enzyme immune assay (Ferrizyme, Abbott Labs, Chicago, USA). The erythrocyte sedimentation rate (ESR) was measured by the Westergren method. The Ritchie index, grip strength, number of swollen joints, morning stiffness and a subjective pain score (visual analogue scale, 0 to 10 points) were assessed as well. Liver and kidney function tests were performed to monitor possible side effects.

Data Evaluation

For evaluation, all clinical data were stored and analyzed on a Wang personal computer using the Lotus 1-2-3 program. Statistical evaluation of the results was by Fishers' exact test for group differences. P values of 0.05 or less were considered significant.

Results

Effect of r-hu-Epo on the Anemia of Chronic Disease (ACD)

In all RA patents, a rise in hemoglobin was observed (Table II). Despite the wide range of values, the increase in hemoglobin became significant after the second week of treatment, compared to baseline values. When treatment was stopped, hemoglobin stayed significantly higher, compared to the baseline value, but dropped in the twelfth week.

Iron deficiency developed, as shown by the fact that five patients were characterized by ferritin levels lower than 40 mg/ml.

Effect of r-hu-Epo on Disease Activity Parameters

Laboratory Parameters: ESR and CRP

A decrease in ESR was found in all patients (Table III), which started at the third week of treatment and remained so until the end of the study. As illustrated, the decrease in eight patients was more than 20% of their baseline value, which was highly significant. The same holds true for the CRP values, but due to the wide range in the absolute values and small number of investigated patients, no significance could be calculated. However, expressing the values as a percentage of the baseline value, in this way after the third week of treatment, a significant decrease in the CRP levels was also observed.

Subjective Clinical Scores: Pain Score (PS) and Morning Stiffness (MS)

Both parameters (PS and MS) showed during the follow-up a tendency to decrease (Table IV). Caused by the variability in absolute values and small number of patients, a significance could not be calculated. When the values were expressed in a percentage of the baseline value, the PS decreased significantly after the third week of treatment and the MS after the sixth week.

Objective Disease Activity Scores: Grip Strength (GS), Ritchie Index (RD and Number of Swollen Joints (SJ)

All parameters as shown in Table V showed a continuous tendency towards improvement that lasted during, and also after, the treatment period. In the absolute changes in number of tender joints, a significant decrease could be calculated from the third week of treatment. Also, a continuous decrease in the number of swollen joints was observed from T3 on and, at T9, nine out of ten patients had less swollen joints, which was highly significant.

Caused by the variation of the individual values of the GS, it was impossible to calculate a significance. However, when the values were expressed as a percentage of their baseline values after three weeks of treatment, a significant increase in GS was noted. It should be mentioned that the GS remained stable in three patients during our investigation.

TABLE I

Demographic features of ten patients characterized on having anemia of chronic disease (ACD) and rheumatoid arthritis (RA)

| Female/Male | 9/1 | |
|---|---|---|
| Mean age (years) | 68 ± 6, 5 | |
| Treatment: | | |
| Prednisolone | (2 patients) | 5 mg |
| Sulphasalasine | (3 patients) (range) | 1.5-2.5 g/day |
| Plaquenil | (1 patient) | 200 mg/day |
| Auromyose | (1 patient) | 50 mg/in 2 weeks |
| D-Penicillamine | (2 patients) (range) | 500-750 mg/day |

All patients were treated for more than two months with the mentioned disease-modifying anti-rheumatic drugs.

TABLE II

Effect of recombinant human erythropoietin (r-hu-Epo) therapy on hemoglobin and ferritin levels at the defined time periods after onset therapy in ten patients with rheumatoid arthritis (RA)

| | Baseline | Values during the 6 weeks therapy and after 3 and 6 weeks of treatment | | | | | | | |
|---|---|---|---|---|---|---|---|---|---|
| Variable | T0* | T1 | T2 | T3 | T4 | T5 | T6 | T9 | T12 |
| Hemoglobin | 5.9 | 6.1 | 6.5** | 6.8 | 7.0 | 7.2 | 7.2 | 7.2 | 6.6 |
| mmol/l ± sd | 0.4 | 0.5 | 0.6 | 0.7 | 0.9 | 1.0 | 1.0 | 1.1 | 0.9 |
| Ferritin material | 216 | | 143** | | | | 80 | 49 | 61 |
| μg/ml range | 140-318 | | 44-301 | | | | 14-157 | 19-82 | 52-84 |

*Refers to treatment week number.
**Marks the treatment period when the differences between baseline became significant.

TABLE III

Effect of recombinant human erythropoietin (r-hu-Epo) treatment on the erythrocyte sedimentation rate (ESR) and C-reactive protein (CRP) levels at the defined time periods after onset therapy in ten patients with rheumatoid arthritis (RA)

| | | Values during 6 and 3 weeks after the end of treatment period | | |
|---|---|---|---|---|
| Variable | Baseline | T3* | T6 | T9 |
| ESR (mmH) | 82 | 61** | 53** | 56** |
| mean ranges | 42-137 | 18-112 | 7-98 | 7-111 |
| ESR (%) | 100 | 63 | 59 | 64 |
| mean ranges | — | 32-107 | 16-108 | 16-144 |
| Number of patients with a change >20% baseline value | — | 8** | 7** | 8** |
| CRP (mg/l) | 51 | 45 | 43 | 44 |
| mean ranges | 10-105 | 4-113 | 3-122 | 1-144 |
| CRP (%) | 100 | 85 | 85 | 81 |
| mean ranges | — | 17-155 | 8-204 | 5-181 |
| Number of patients with a change >20% baseline value | — | 5** | 6** | 6** |

*Refers to treatment week number.
**Marks the treatment period when the differences compared to baseline values became significant.
P > 0.05, Fishers' exact test.

TABLE IV

Effect of recombinant human erythropoietin (r-hu-Epo) treatment on the overall pain score (PS) and morning stiffness duration (MS) at the defined time periods after onset treatment in ten patients with rheumatoid arthritis (RA).

| | | Values during 6 and 3 weeks after the end of treatment period | | |
|---|---|---|---|---|
| Variable | Baseline | T3* | T6 | T9 |
| PS | 3.9 | 3.0 | 2.7 | 2.8 |
| mean ranges | 2.7 | 1-5 | 1-5 | 1-5 |
| PS (%) | 100 | 82 | 70 | 73 |
| mean ranges | — | 50-150 | 33-150 | 33-100 |
| Number of patients with a change >20% baseline value | — | 7** | 8** | 6** |
| MS (min) | 45 | 37 | 35 | 36 |
| mean ranges | 10-120 | 10-120 | 10-120 | 10-120 |
| MS (%) | 100 | 88 | 78 | 85 |
| mean ranges | — | 50-150 | 50-150 | 50-150 |

TABLE IV-continued

Effect of recombinant human erythropoietin (r-hu-Epo) treatment on the overall pain score (PS) and morning stiffness duration (MS) at the defined time periods after onset treatment in ten patients with rheumatoid arthritis (RA).

| Variable | Baseline | Values during 6 and 3 weeks after the end of treatment period | | |
|---|---|---|---|---|
| | | T3* | T6 | T9 |
| Number of patients with a change >20% baseline value | — | 3 | 5** | 5** |

*Refers to treatment week number.
**Marks the treatment period when the differences compared to baseline values became significant.
P > 0.05, Fishers' exact test.

TABLE V

Effect of recombinant human erythropoietin (r-hu-Epo) treatment on the Ritchie index (RI), number of swollen joints (SJ) and grip strength (GS) at the defined time periods after onset treatment in ten patients with rheumatoid arthritis (RA)

| Variable | Baseline | Values during 6 and 3 weeks after the end of treatment period | | |
|---|---|---|---|---|
| | | T3* | T6 | T9 |
| RI | 13 | 10.2 | 7.7** | 6** |
| mean ranges | 3-38 | 1-22 | 1-14 | 2-13 |
| RI (%) | 100 | 66 | 62 | 56 |
| mean ranges | — | 25-100 | 33-111 | 22-95 |
| Number of patients with a change >20% baseline value | — | 8** | 7** | 9** |
| SJ | 8 | 6 | 4.5 | 4.5 |
| mean ranges | 6-5 | 3-11 | 2-8 | 1-9 |
| SJ (%) | 100 | 72 | 61 | 51 |
| mean ranges | — | 42-100 | 37-100 | 20-100 |
| Number of patients with a change >20% baseline value | — | 8* | 7* | 9* |
| erythrocyte sedimentation rate (ESR) (mmH) | 72 | 87 | 91 | 90 |
| | 15-190 | 20-220 | 20-220 | 15-220 |
| mean ranges | 100 | 112 | 118 | 118 |
| ESR (%) | | | | |
| mean ranges | — | 90-133 | 90-166 | 90-166 |
| Number of patients with a change >20% baseline value | — | 4** | 4** | 5** |

*Refers to treatment week number.
**Marks the treatment period when the differences compared to baseline values became significant.
P > 0.05, Fishers' exact test.

References

1. Mowat M. G. Hematologic abnormalities in rheumatoid arthritis. *Semin. Arthr. Rheum.* 1:383-390 (1971).
2. Hansen T. M., H. E. Hansen, H. S. Birgens, B. Holund, I. Lorenzen. Serum ferritin and the assessment of iron deficiency in rheumatoid arthritis. *Scand. J. Rheumatol.* 12:353-359 (1983).
3. Vreugdenhil G., C. A. M. Baltus, H. G. Van Eijk, A. J. G. Swaak. Anemia of chronic disease. Diagnostic significance of erythrocyte and serological parameters in iron-deficient rheumatoid arthritis patients. *Br. J. Rheumatol.* 29:105-110 (1990).
4. Couchman K. G., L. Bieder, R. D. Wigley, A. G. Glenday. Vitamin B12 absorption and gastric antibodies in rheumatoid arthritis. *NZ Med. J.* 153-156 (1968).
5. Vreugdenhil G., A. W. Wognum, H. G. Van Eijk, A. J. G. Swaak. Anemia in rheumatoid arthritis. The role of iron, vitamin B12 and folic acid deficiency and erythropoietin responsiveness. *Ann. Rheum. Dis.* 49:93-98 (1990).
6. Van de Putte L. B. A. Pancytopenia related to azathioprine in rheumatoid arthritis. *Ann. Rheum. Dis.* 47(6):503-505 (1988).
7. Dinant H. J., C. E. M. De Maat. Erythropoiesis and mean cell lifespan in normal subjects and patients with the anemia of rheumatoid arthritis. *Br. J. Hematol.* 39:437-444 (1979).
8. Cartwright G. E. and G. R. Lee. The anemia of chronic disorders. *Br. J. Hematol.* 21:147-152 (1971).
9. Williams R. A., D. Samson, J. Tikerpae, H. Crowne, J. M. Gumpel. In vitro studies of ineffective erythropoiesis in rheumatoid arthritis. *Ann. Rheum. Dis.* 41:502-507 (1982).
10. Maury C. P. J., L. C. Andersson, A. M. Teppo, S. Patanen, E. Juronen. Mechanisms of anemia in rheumatoid arthritis: demonstration of raised interleukin-1 beta concentrations in anemic patients and of interleukin-1 beta-mediated suppression of normal erythropoiesis and proliferation of human erythroleukemia cells in vitro. *Ann. Rheum. Dis.* 47:972-978 (1988).
11. Roodman G. D. Mechanisms of erythroid suppression in anemia of chronic disease. *Blood Cells* 13:171-184 (1987).
12. Ward H. P., B. Gordon, J. C. Picket. Serum levels of erythropoietin in rheumatoid arthritis. *J. Lab. Clin. Med.* 74:93-97 (1969).
13. Baer A. N., N. Dessypris, E. Goldwasser, S. B. Krantz. Blunted erythropoietin response to anemia in rheumatoid arthritis. *Br. J. Hematol.* 66:559-564 (1987).
14. Zucker S., R. M. Lysik, M. Di Stefano. Cancer cell inhibition on erythropoiesis. *J. Lab. Clin. Med.* 99:770-782 (1980).
15. Harvey A. R., B. J. Clarke, D. H. K. Chui, F. Kean, W. W. Buchanan. Anemia associated with rheumatoid disease. Inverse correlation between erythropoiesis and both IgM and rheumatoid factor levels. *Arthr. Rheum.* 26:28-34 (1983).
16. Esbach J. W., J. C. Egrie, M. R. Downing. Correction of the anemia of endstage renal disease with recombinant human erythropoietin results of a phase I an II clinical trial. *N. Eng. J. Med.* 316:73-78 (1987).
17. Urabe A., F. Tokaku, N. Mimura. Therapeutic effect of recombinant human erythropoietin in anemia caused by chronic renal disease. *Exp. Hematol.* 15:438-441 (1987).
18. Ponticelli C., S. Casat. Correction of anemia with recombinant human erythropoietin. *Nephron.* 52:201-208 (1989).
19. Fischl M., J. E. Galpin, J. D. Levine. Recombinant human erythropoietin for patients with AIDS treated with Zidovudine. *N. Eng. J. Med.* 21:1488-1493 (1990).
20. Pincus T., N. J. Olsen, I. J. Russel. Multicenter study of recombinant human erythropoietin in correction of anemia in rheumatoid arthritis. *Am. J. Med.* 89:161-168 (1990).
21. Vreugdenhil G., B. Manger, C. Nieuwenhuizen, H. G. van Eijk, A. J. G. Swaak. Iron stores and serum transferrin receptor levels during recombinant human erythropoietin treatment of anemia in rheumatoid arthritis. *Ann. of Hematol.* 65:265-268 (1992).
22. Arvett F. C., S. Edworthy, D. E. Bloch. The American Rheumatism Association 1987, revised criteria for the classification of rheumatoid arthritis. *Arthr. Rheum.* 31:315-324 (1988).
23. Vreugdenhil G. and A. J. G. Swaak. "Synovial Iron Deposition and Rheumatoid Arthritis" in *Handbook on Metal-*

*Ligand Interactions in Biological Fluids*, Vol. 2 Part Four, Chapter 5 Section C. Editor: Guy Berthon (1993).

What is claimed is:

1. A method for treatitng chronic inflammation in a subject, the method comprising:
   identifying that the subject is suffering from chronic inflammation, and
   administering to the subject means for providing erythropoietin-like activity in order to reduce the chronic inflammation,
   wherein the means for providing erythropoietin-like activity is human erythropoietin.

2. A method for treating a subject suffering from at least one symptom of rheumatoid arthritis, the symptom selected from the group consisting of morning stiffness, painful joints, swollen joints, loss of grip strength, and pain, the method comprising:
   identifying that the subject is suffering from the at least one symptom of rheumatoid arthritis; and
   administering to the subject means for providing erythropoietin-like activity in order to treat the at least one symptom of rheumatoid arthritis in the subject,
   wherein the means for providing erythropoietin-like activity is human erythropoietin.

* * * * *

UNITED STATES PATENT AND TRADEMARK OFFICE
CERTIFICATE OF CORRECTION

| | | |
|---|---|---|
| PATENT NO. | : 9,155,782 B2 | Page 1 of 1 |
| APPLICATION NO. | : 11/811665 | |
| DATED | : October 13, 2015 | |
| INVENTOR(S) | : Anthonius Josef Swaak | |

It is certified that error appears in the above-identified patent and that said Letters Patent is hereby corrected as shown below:

In the specification:

COLUMN 1,   LINE 8,    change "of U.S." to --of co-pending U.S.--
COLUMN 5,   LINE 20,   change "Index (RD and" to --Index (RI and--

In the claims:

CLAIM 1,   COLUMN 9,   LINE 4,   change "method for treatitng" to --method for treating--

Signed and Sealed this
Seventeenth Day of May, 2016

Michelle K. Lee
*Director of the United States Patent and Trademark Office*